United States Patent [19]

Barker et al.

[11] Patent Number: 4,587,617
[45] Date of Patent: May 6, 1986

[54] IMAGE INSPECTION SYSTEM FOR DEFECT DETECTION

[75] Inventors: John C. Barker, Oakington; Ian A. Cruttwell, Great Chishall, Nr. Royston, both of England

[73] Assignee: Cambridge Instruments Limited, Cambridge, England

[21] Appl. No.: 543,038

[22] Filed: Oct. 18, 1983

[30] Foreign Application Priority Data

Nov. 2, 1982 [GB] United Kingdom ............... 8231268

[51] Int. Cl.$^4$ .................. G06F 15/70; G06K 9/46
[52] U.S. Cl. .................... 364/507; 356/237; 358/106; 358/107; 382/34
[58] Field of Search ............. 364/507, 514; 382/8, 382/34, 44, 54, 55; 358/106, 107; 356/237

[56] References Cited

U.S. PATENT DOCUMENTS

| | | | |
|---|---|---|---|
| 4,345,312 | 8/1982 | Yasuye et al. | 382/8 |
| 4,377,340 | 3/1983 | Green et al. | 356/237 |
| 4,403,294 | 9/1983 | Hamada et al. | 364/507 |
| 4,417,149 | 11/1983 | Takeuchi et al. | 356/237 X |
| 4,430,749 | 2/1984 | Schardt | 382/54 |
| 4,442,542 | 4/1984 | Lin et al. | 382/8 |
| 4,445,185 | 4/1984 | Davis, Jr. et al. | 364/514 |
| 4,454,542 | 6/1984 | Miyazawa | 358/106 |
| 4,479,145 | 10/1984 | Azuma et al. | 358/106 |
| 4,481,664 | 11/1984 | Linger et al. | 382/8 |
| 4,496,971 | 1/1985 | West et al. | 358/106 |

FOREIGN PATENT DOCUMENTS

| | | |
|---|---|---|
| 1046443 | 10/1966 | United Kingdom . |
| 1328121 | 8/1973 | United Kingdom . |
| 1391056 | 4/1975 | United Kingdom . |
| 1445685 | 8/1976 | United Kingdom . |

Primary Examiner—Felix D. Gruber
Attorney, Agent, or Firm—Leydig, Voit & Mayer

[57] ABSTRACT

A defect detection system for classifying defects in reticles (such as used in the manufacture of integrated circuit wafers) is described. An inspection unit, scanning the reticle in real time, compares it with the correct form and inputs signals representing each defect and its position in a store. The stored defects are then used to direct the inspection unit to inspect each defect more slowly. The inspection unit classifies each defect as either being an "excess metal" or a "missing metal" defect, and corresponding signals are stored in respective additional stores. The signals stored in these stores are then further processed and compared with the desired form of the reticle so as to classify the "excess metal" defects as either being a "pin spot" defect, an "extension" defect or a "bridge-type" defect. Similarly, the "missing metal" defects are classified as either being a "pinhole" defect an "intrusion" defect or a "break-type" defect. A size measuring unit measures the size of each defect.

13 Claims, 29 Drawing Figures

IMAGE INSPECTION SYSTEM FOR DEFECT DETECTION

BACKGROUND OF THE INVENTION

The invention relates to inspection systems. Embodiments of the invention to be described below involve the inspection of images, the location of errors or faults therein, and the classification and/or measurement of the errors. For example, the images may be images produced by manufactured products and the errors may be errors introduced by the manufacturing process. Thus, for example, the invention may be used in the inspection of reticles in the form of glass plates on which are formed metal patterns, these reticles being intended for use subsequently in the manufacture of integrated circuit wafers, the metal patterns defining electrical connections on the wafers. It is therefore important to ensure that each reticle is free of significant faults, because such faults may be repeated in the integrated circuit wafers produced from the reticles.

SUMMARY OF THE INVENTION

According to the invention, there is provided an image system in which abnormalities in the image are noted automatically and automatically classified as to type by comparing the actual image with a desired form thereof.

According to the invention, there is further provided an image inspection system for inspecting an image in the form of a desired predetermined pattern of image paths with spaces between them comprising first classification means for automatically inspecting the image, comparing it with the desired form of the image, and storing data identifying the position and size of each abnormality of addition and of each abnormality of omission, second classification means responsive to each abnormality of addition for automatically classifying it as an abnormality of addition in a said space and unconnected with any said path, an abnormality of addition in a said space and connected to one said path, or an abnormality of addition in a said space and connected to two said paths, and third classification means for automatically classifying each abnormality of omission as an abnormality of omission within a said path but not completely breaking the path, an abnormality of omission in an edge, only, of a said path or an abnormality of omission within and completely breaking a said path.

According to the invention, there is still further provided a method of inspecting an image, comprising the steps of carrying out a relatively rapid inspection of the whole image so as to detect the existence of any abnormalities therein and at least the approximate position of those abnormalities by comparing the actual image with a desired form thereof, and carrying out relatively less rapidly an inspection of those parts of the image where abnormalities have been noted by the first inspection step to classify those abnormalities as to type and to measure their sizes.

According to the invention, there is yet further provided a method of inspecting an image in the form of a predetermined pattern of image paths with spaces between them comprising the steps of automatically inspecting the image, comparing it with the desired form of the image, and storing data identifying the position and size of each abnormality of addition and of each abnormality of omission, automatically classifying each abnormality of addition as being either an abnormality of addition in a said space and unconnected with any said path, an abnormality of addition in a said space and connected to one said path or an abnormality of addition in a said space and connected to two said paths, and automatically classifying each abnormality of omission as being either an abnormality of omission within a said path but not completely breaking the path, an abnormality of omission in an edge, only, of a said path, or an abnormality of omission within and completely breaking a said path.

DESCRIPTION OF THE DRAWINGS

A reticle inspection system embodying the invention will now be described by way of example and with reference to the accompanying drawings, in which.

DESCRIPTION OF PREFERRED EMBODIMENT

Figure 1:
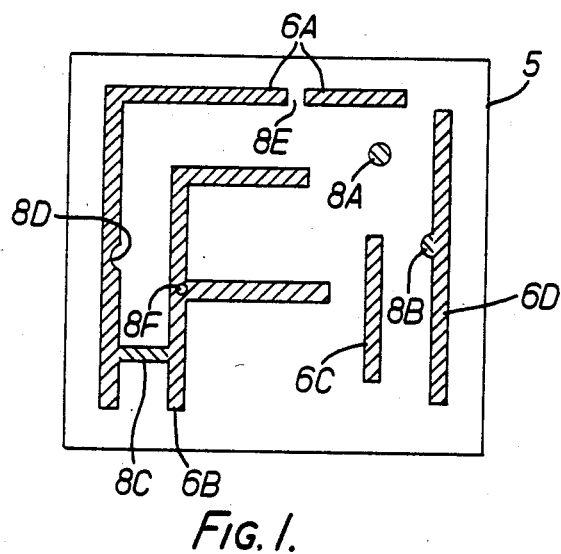
FIG. 1 shows in diagrammatic form a reticle to be inspected with various forms of possible defects.

FIG. 1 shows in diagrammatic form a simplified version of a reticle to be inspected. This is a glass plate 5 on which is formed a pattern of metal paths 6A, 6B, 6C and 6D. The paths constituting the patterns may be made of chromium for example. The process of manufacturing the reticle, which does not form part of the present invention, may inevitably produce faults occasionally, and these faults can be of various different types. For example, one possible fault is a "pin spot" 8A being a small portion or "spot" of metal which has been inadvertently deposited on the glass plate. Another possible fault is shown at 8B, this being termed an "extension" and being in the form of additional metal extending from and connected to one of the metal paths, (path 6D). Another possible fault is a "bridge" as shown at 8C, this being erroneously deposited additional metal which bridges between two metal paths (6A and 6B). At 8D is shown an "intrusion" where there has been a failure to deposit sufficient metal to provide the full width of the metal path. Another possible fault is shown at 8E, this being a "break" where, again, that has been a failure to deposit sufficient metal, but this time the failure is such as to completely separate the metal path (6A).

Finally, at 8F is shown a "pinhole" where there is an inadvertent absence of deposited metal within the width of one of the metal paths (6B). In a manner to be described, the system inspects each reticle, automatically locates faults such as those described above, measures their sizes, and classifies each fault as being a particular one of the six types specified above. The operator is then provided with a read-out of the results of the inspection, this read-out being given in any suitable way such as by means of a computer print-out. He can then consider the results of the inspection and decide whether or not to reject the reticle or take other steps.

The inspection process is carried out in two stages, the first of which will now be described in reference to FIG. 2.

Figure 2:
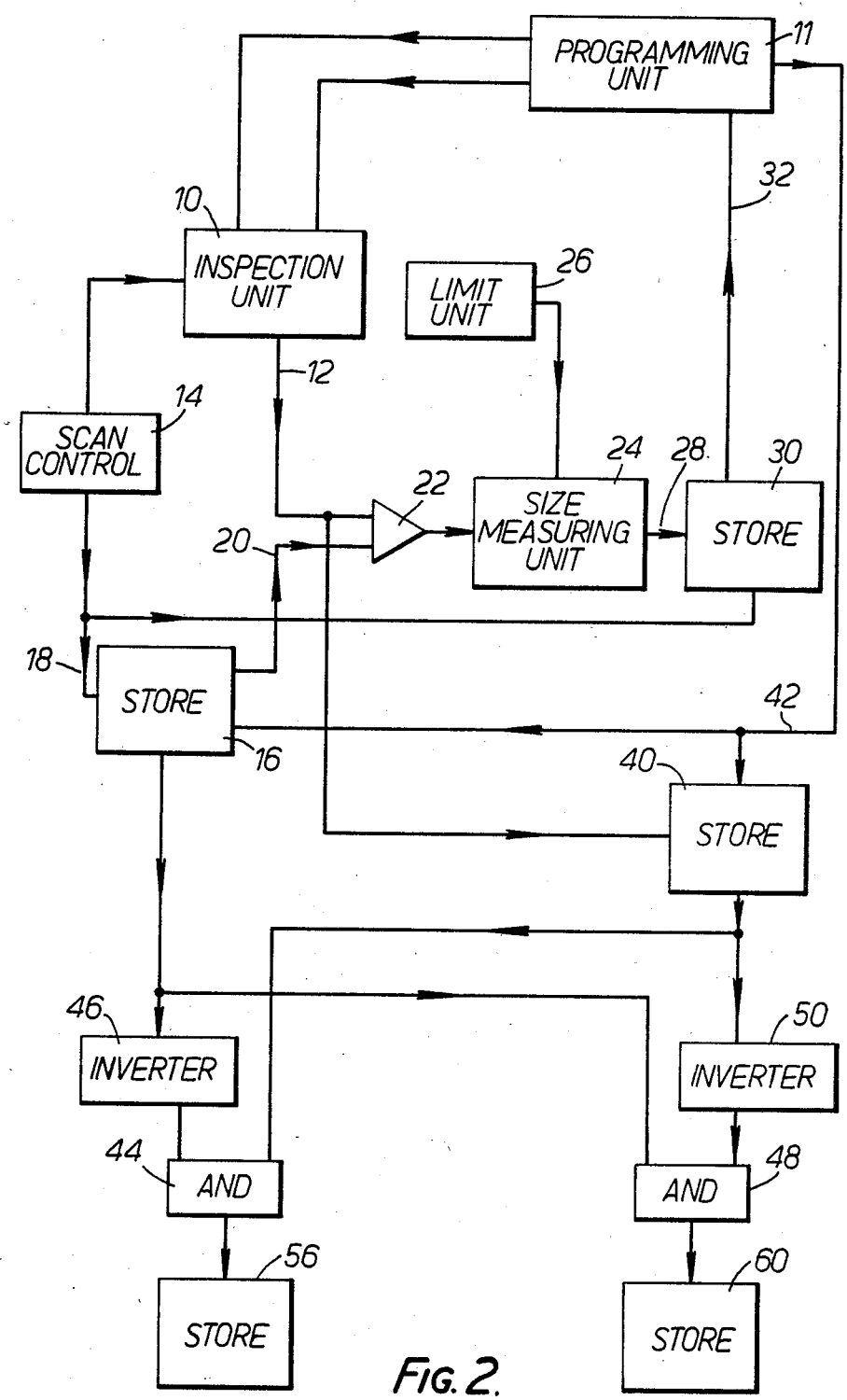
FIG. 2 is a block diagram of part of the systems.

As shown in FIG. 2, the inspection system has an inspection unit 10 of any suitable form which scans the reticle or an image of the reticle and optically measures the pattern on it. For example, it may comprise means for scanning the reticle to produce an output on a line 12 whose binary state is instantaneously representative of the part of the reticle currently being inspected—that is, indicating whether or not metal is present. The scanning carried out by the inspection unit 10 is carried out under control of a programming unit 11 and a scan control unit 14. A store 16 stores a representation of the exact desired form of the image, this being stored by means of electrical digital signals each of which corresponds to a particular location on the reticle and whose value indicates whether or not metal is present there. The digital signals in the store 16 may, for example, be the same digital signals which are used during the manufacturing process to produce the reticle itself. The scan control unit 14 not only controls the inspection unit 10 but also activates the store 16 by means of a line 18 so that the store 16 outputs on a line 20 the digital signal indicating the desired state of the reticle at each point as it is inspected by the inspection unit 10. The digital signals on the line 12 and 20 are fed into a comparator 22. Provided that there is no difference between the two signals, the comparator produces zero output, this of course indicating no defect in the reticle. However, if there is a defect in the reticle this will cause the comparator 22 to produce a digital signal. This is passed to a size measuring unit 24 which is controlled by a limit setting unit 26. The purpose of the unit 24 is to measure the size of the defect by counting the number of consecutive digital signals produced by the comparator 22. The limit setting unit 26 is controllable by the operator when the system is set up and by means of this unit the operator inputs a minimum defect size. Only if the unit 24 determines that a defect is greater than the minimum size, does this produce an error signal on a line 28 which is fed into a store 30 and stored there in a storage location corresponding to the location of the defect in the reticle. In practice the system is arranged so that the store 30 does not note the exact location of each defect but merely notes whether or not there are any defects (above the minimum size) in each of successive "fields" of the reticle, each such field being a small part of its total area.

The purpose of the process just described is not to measure or classify the defects (except to respond only to those above the minimum size) but simply to determine whether or not there are any significant defects and to indicate their location. Advantageously, this process is carried out very rapidly, in real time preferably, so that any fault-free reticle is immediately available for use. The inspection process just described may advantageously (though not necessarily) employ the image comparison system described in the co-pending U.S. patent application Ser. No. 543,037.

The second stage of the inspection process is for inspecting those fields of the reticle where defects have been noted and classifying and measuring those defects.

The first part of the second stage of the inspection process involves the classification of each error to determine whether it is a defect of "excess metal" or a defect of "missing metal". Defects of excess metal are pin spot defects (e.g. defect 8A, FIG. 1), extension defects (defect 8B) and bridge defects (defect 8C). Defects of missing metal are intrusion defects (defect 8D), bridge defects (defect 8E) and pin hole defects (defect 8F).

During the second inspection stage, the store 30 directs the inspection unit 10 in turn to each of the fields of the reticle where a defect has been detected during the first inspection stage, and a complete inspection process (to be described below) is carried out on that field before any other field containing a defect is inspected. The store 30 directs the inspection unit 10 to a field having a defect by means of signals on a line 32 to the programming unit 11.

The inspection unit 10 then carries out a scan of the field and digital signals representing the image of this field are stored in a "live image" store 40. When a complete scan of the field has taken place, the programming unit 11 activates the store 16 and the store 40, by means of a control line 42, so that the store 40 outputs its stored image serially, that is, it outputs serially the digital signals defining the stored image. Simultaneously with this, the store 16 outputs its stored image of the field, that is the correct form of the field. The digital signals from store 16 are fed to the input of an AND gate 44 through an inverter 46 and are also fed uninverted to one input of an AND gate 48. The digital signals from the store 40 are fed uninverted to the second input of the AND gate 44 and are fed through an inverter 50 to the second input of the AND gate 48.

Figure 3A:
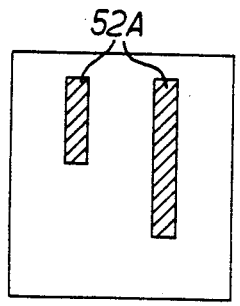
FIGS. 3A, 3B, 3C and 4A, 4B, 4C are diagrams for use in explaining the operation of the system of FIG. 2.
Figure 3B:
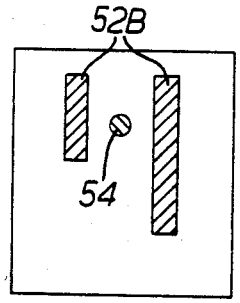
Figure 3C:
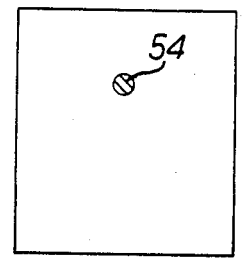

FIGS. 3 and 4 explain the operation as so far described. FIG. 3A shows the image which is assumed to be stored in store 16 and representing the desired pattern in the field under inspection. It will be apparent that the desired pattern consists of two metal paths 52A. FIG. 3B shows the pattern which is assumed to be stored in the store 40, being the actual (erroneous) image in this particular field. As shown, it consists of two metal paths 52B, corresponding exactly to the metal paths 52A, and an erroneous pin spot 54. It will be apparent that the effect of the inverter 46 and the AND gate 44 is to invert the image of FIG. 3A and add it to the image of 3B. The result will be the production of digital signals representing the image shown in FIG. 3C, thus consisting only of the excess metal forming the pin spot 54. The output of the AND gate 44 is fed into an excess metal store 56 (FIG. 2) and the image which it stores, represented in digital form, is thus what is shown in FIG. 3C.

Figure 4A:
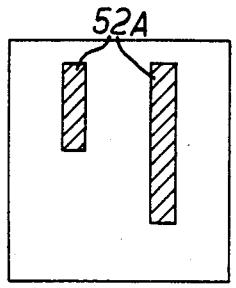
Figure 4B:
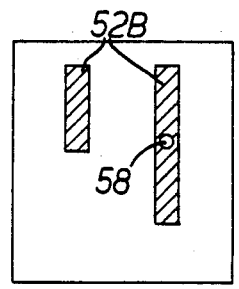

FIG. 4 illustrates the operation carried out by the AND gate 48. Here, it is assumed that the image stored in the store 16 for the field under inspection is as shown in FIG. 4A (that is, identical with what is shown in FIG. 3A). The image shown in store 40 is assumed to be that illustrated in FIG. 4B. As shown, this consists of metal conductors 52B identical with conductors 52A but it also includes a pin hole 58 where there is omission of metal.

Figure 4C:
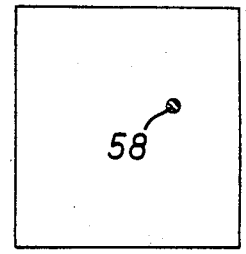

The effect of the inverter 50 and the AND gate 48 of FIG. 2 is to invert the image shown in FIG. 4B and add it to the image shown in FIG. 4A, and the result produced is as shown in FIG. 4C, that is a spot representing the pin hole 58. The digital signals representing this image are fed out by the AND gate 48 and stored in a store 60 (FIG. 2).

The operation is basically similar for the other types of defect described above. Therefore, the store 56 stores defects consisting of excess metal (pin spot, extension and bridge type errors), and store 60 stores errors consisting of missing metal (that is, pin hole, intrusion and break type errors).

It will be appreciated that each of the stores 56 and 60 may store data representing more than one defect, if there should be more than one defect in the field of the image under inspection.

Figure 5:
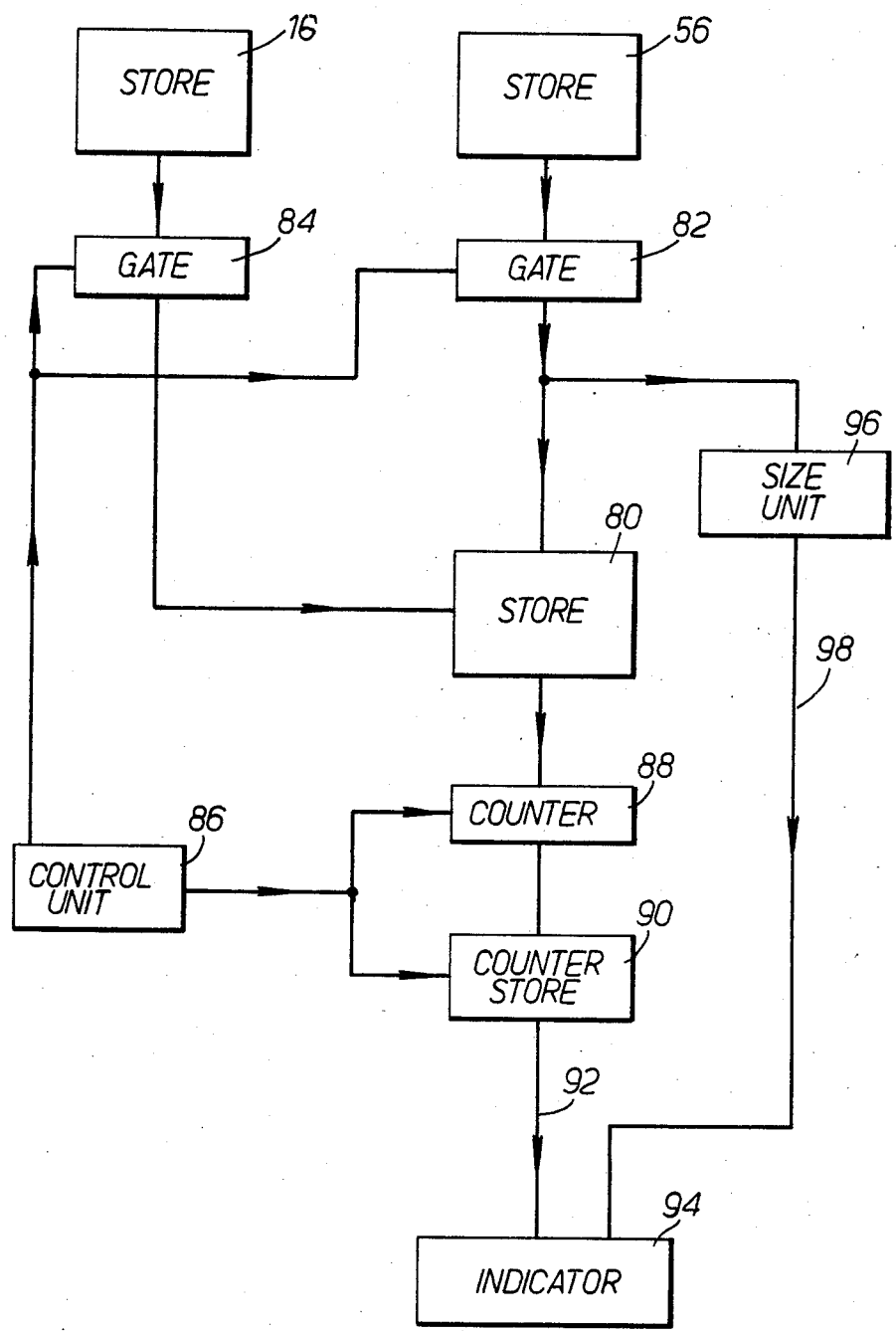
FIG. 5 is a block diagram of a further part of the system.

FIG. 5 shows the part of the system which is used to process the data in the store 56 in order to determine whether the or each defect therein is a pin spot, an extension or a bridge type defect.

FIG. 5 shows that the stores 16 and 56 of FIG. 2, that is the stores storing the desired form of the total image and the "excess metal" defect(s) in the field under inspection.

As shown in FIG. 5, the part of the system under discussion has a store 80 into which the contents of the store 56 can be passed through a gate 82. However, the gate 82 is arranged such that only one of the defects in the store 56 (if in fact the latter stores more than one) can be passed into the store 80 at a time.

The store 80 can also receive the contents of the store 16 relating to the particular field under investigation, this data being passed through a gate 84. The gates 82 and 84 are controlled by a control unit 86.

FIG. 6 explains the operation of the system.

Figure 6A:
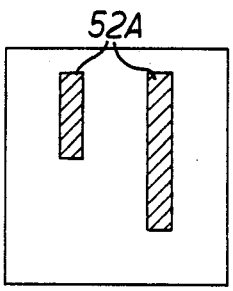
FIGS. 6A–6G show diagrams for explaining the operation of the part of the system shown in FIG. 5.

FIG. 6A shows the assumed contents of that part of the store 16 relating to the image field under consideration, and, as shown, it is assumed to be storing data corresponding to two metal paths 52A, that is, identical to what is shown in FIGS. 3A and 4A.

Figure 6B:
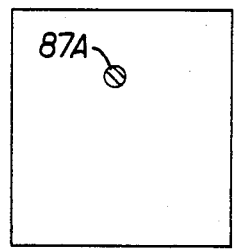
Figure 6C:
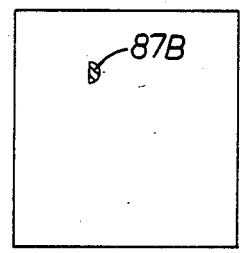
Figure 6D:
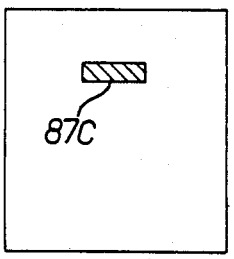

FIGS. 6B, 6C and 6D show examples of images of defect which could be represented by the data stored in the "excess metal" store 56. Defect 87A is a pin spot, defect 87B is an extension, and defect 87C is a bridge.

In operation, the control unit 86 opens the gate 84 and feeds into the store 80 the data in store 16 relating to the field under investigation, this data being as shown in FIG. 6A. The store 80 is otherwise empty. The control unit 86 now activates a counter 88 to count the number of "features" in the store 80. A single "feature" is data representing a number of connected image points. Thus, each metal path 52A shown in FIG. 6A is made up of a large number of image points which are all immediately adjacent to each other, that is, connected to each other, and therefore representing a single "feature". The counter 88 will therefore come to a count of two, because the metal paths 52A which are now stored in store 80 constitute two "features". The control unit 86 now transfers this count of two into a counter store 90 and clears the counter 88.

Figure 6E:
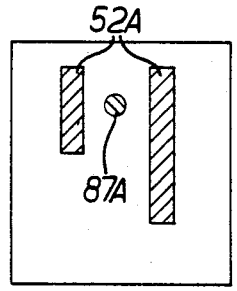

The control unit now opens the gate 82 and the data in store 56 (that is, as shown in FIG. 6B) is now loaded into the store 80 in superimposition on the data already stored therein. The data now in store 80 is therefore as shown in FIG. 6E. Counter 88 is now activated to count the number of features, and this time the count will be three, the individual features being the metal paths 52A and the defect 87A shown in FIG. 6B. This count will be entered into the store 90 which will determine that the count has therefore increased by one.

Figure 6F:
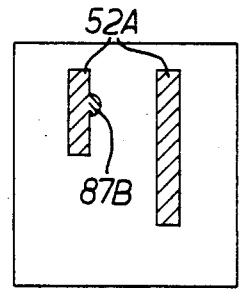

It will now be assumed that the above process is carried out for the defect shown in FIG. 6C. Store 80 is cleared and the data shown in FIG. 6A is loaded into the store 80. Counter 88 will therefore store a count of two in the store 90 as before. The data shown in FIG. 6C is loaded into the store 80 and the result will be as shown in FIG. 6F—because defect 87B as shown in FIG. 6C is an extension. Counter 88 is reset. Because an extension is by definition excess metal which is joined on to an existing feature, counter 88 will reach a count of two again, when reactivated to count the number of features now in the store. When this is input into the store 90, the latter will thus determine that there has been no change in the number of features.

Finally, the processing of the defect shown in FIG. 6D will be considered.

Figure 6G:
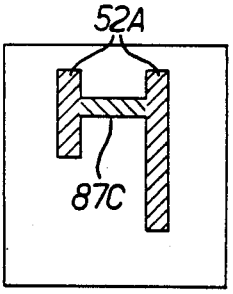

Initially store 80 is cleared and the data (FIG. 6A) in store 16 is input into the store 80 and the counter 88 will count the number of features as two which will be passed into the count store 90. Gate 82 is now opened to superimpose the data shown in FIG. 6D into store 80 which will therefore now be storing what is shown in FIG. 6G. The counter 88 will now be re-activated to count the number of features in the store 80 and this time the count will be one, because the defect 87C has had the effect of joining together the two separate features represented by the two conductors 52A. The counter store 90 will therefore determine the number of features has decreased by one.

From the foregoing, it will be therefore noted that a pin spot-type defect is indicated when the counter store 90 measures an increase (by one) in the number of features in the store 80 as a result of the entry of the data from store 56 into the store 80, an extension-type defect is indicated by no change in the number of features, and a bridge-type defect is indicated by a reduction by one in the number of features. The counter store 90 has an output line 92 which feeds an indicator 94 with data indicating whether there has been an increase, no change or a decrease in the number of features, and the indicator 94 indicates the type of defect accordingly.

In addition, the system includes a size measuring unit 96 which responds to the data being transmitted from the store 56 into the store 80 and measures its size by measuring the number of digital signals making up the defect. The resultant output is fed into the indicator 94 by a line 98 and indicated in suitable form, e.g. in microns.

Therefore, the indicator 94 produces an indication in any suitable form (e.g. visually or by means of a printout) indicating the type of defect and its size.

Figure 7:
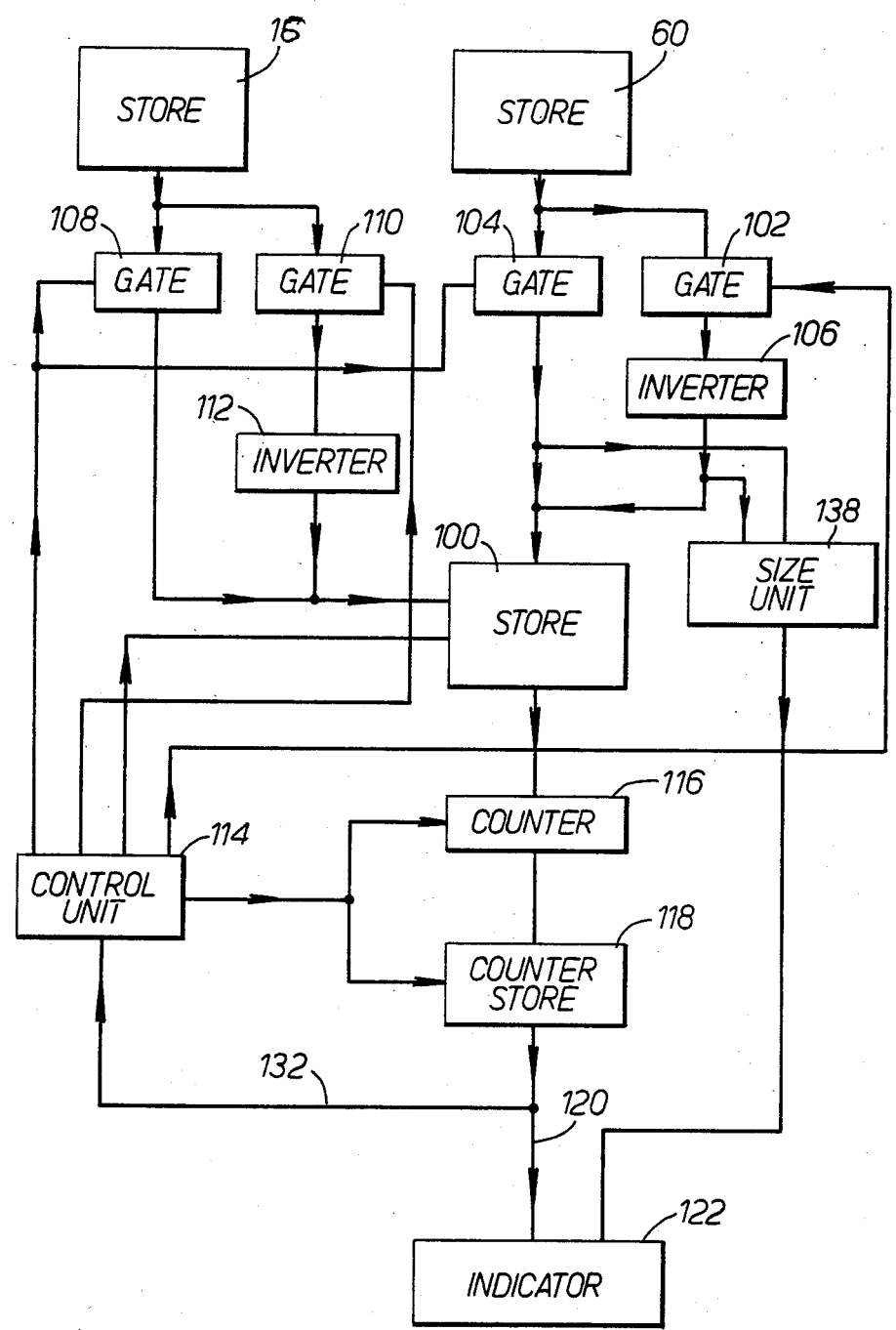
FIG. 7 is a block diagram of another part of the system.

FIG. 7 shows the part of the system for processing the data in the "missing metal" store 60 of FIG. 2.

FIG. 7 repeats the store 60 and store 16 of FIG. 2.

FIG. 7 shows a store 100 to which the store 60 is connected via two paths through gates 102 and 104 respectively, the connection via gate 102 being through an inverter 106 and the connection through gate 104 being direct. Similarly, store 16 is connected to the store 100 through two gates, gates 108 and 110, the connection via gate 108 being direct and the connection via gate 110 being through an inverter 112. The gates 102, 104, 108, 110 are controlled by a control unit 114.

Figure 8:
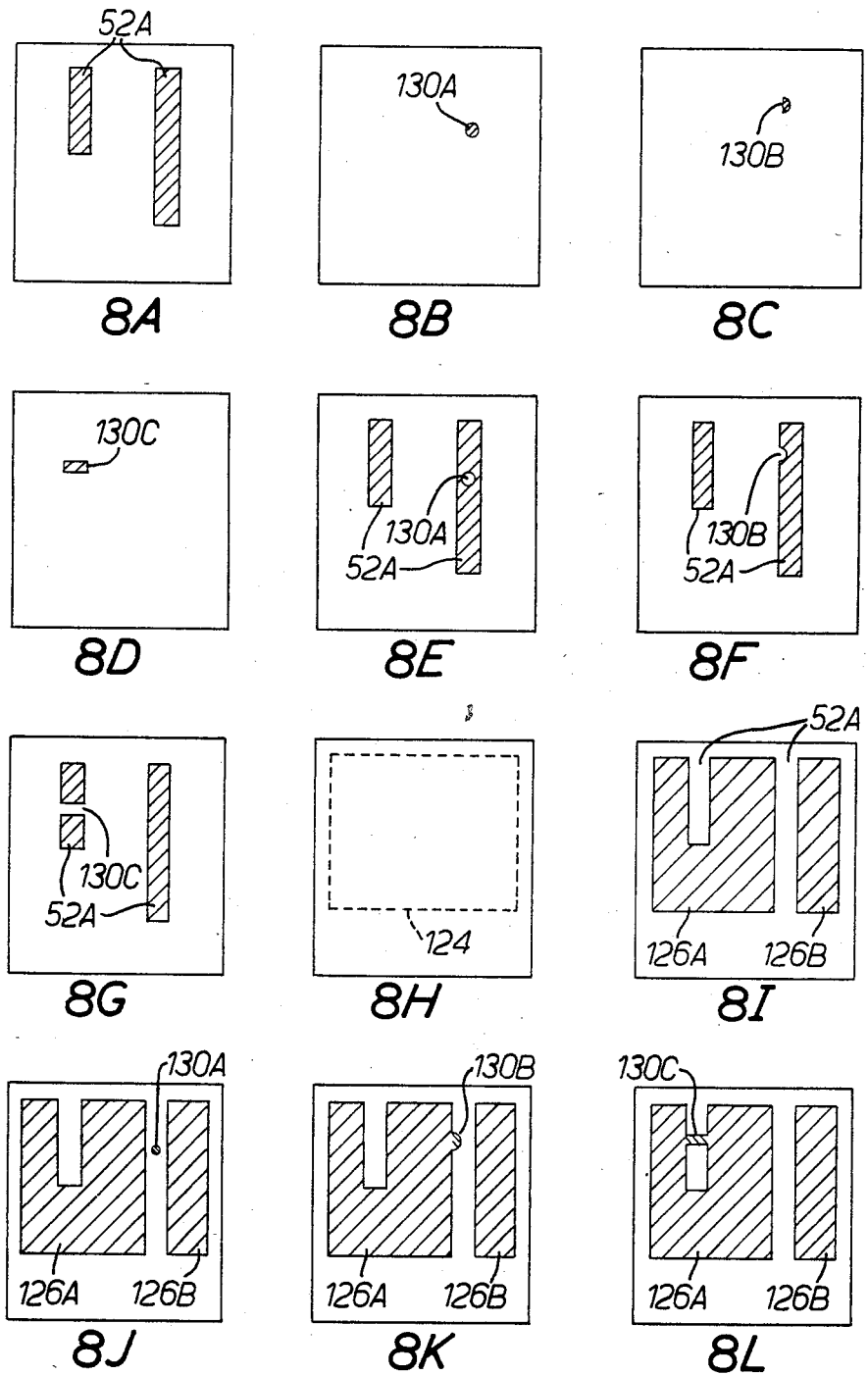
FIGS. 8A–8L show diagrams for explaining the operation of the part of the system shown in FIG. 7.

The operation of the system shown in FIG. 7 will now be described, with particular reference to FIG. 8. FIG. 8A shows the image which is assumed to be stored in store 16 and relating to the particular field under investigation, and is in this case assumed to be two metal paths 52A, similar to that shown in FIG. 4A. FIGS. 8B, 8C and 8D show different forms of defect which might be stored in the store 56. The defect 130A shown in FIG. 8B is a pin hole type defect, the defect 130B shown in FIG. 8C is an intrusion-type defect and the defect 130C shown in FIG. 8D is a break-type defect.

In operation, the control unit 114 initially opens gate 108 (FIG. 7) and the image shown in FIG. 8A is fed into store 100 which was previously empty. The control unit 114 activates a counter 116 to count the number of "features" (as defined above) in the store 100 and therefore a count of two will be recorded. This is stored in a counter store 118. The counter is then cleared. Gate 102 is then opened. As explained above, the store 60 may store data relating to more than one defect. However, the gate 102 is arranged such that the data relating only to one defect is allowed to pass through at a time. It will therefore be assumed that the data passing through is the data representing the image shown in FIG. 8B. This data is inverted by the inverter 106 and then superimposed on the image already in the store 100. The result will therefore be as shown in FIG. 8E, thus being the image of the two metal paths 52A one having the pin hole 130A within it. Counter 116 will now be activated and will again count the number of features as two and this will be noted by the counter store 118.

Store 100 is now cleared and the data in store 16 (FIG. 8A) is now re-entered into store 100, again through gate 108. Counter 116 counts the number of features as two which is stored by the store 118. The counter is reset. Gate 102 is again re-opened and the defect 130B shown in FIG. 8C is now entered through inverter 106 into the store 100 which thus now stores an image as shown in FIG. 8F, being the image of the conductor 52A with the intrusion 130B in it. Again, the counter 116 is activated and again counts the number of features as two, that is, as before.

Store 100 is then cleared again and the data in store 16 (FIG. 8A) is then re-entered into store 100, again through gate 109. Counter 116 counts the number of features as two which is stored by the store 118. The counter is reset.

Gate 102 is then re-opened and the data represented by FIG. 8D is inverted and superimposed on the data in store 100, thus producing the image shown in FIG. 8G, this time showing one of the paths 52A split by the break 130C. The counter 116 now re-counts the number of features and will now reach a count of three, one more than before. The counter store 118 thus determines that the number of features counted has increased by one, and outputs a signal accordingly on a line 120 to an indicator 122 to indicate that the defect is a break-type defect.

Counter store 118 does not produce an output on line 120 during the process described above when there has been a decrease or no change in the number of features counted. In other words, this part of the process will produce an indication on line 120 if the defect is a break-type defect but will produce no such indication if the defect is not a break-type defect. The latter determination is carried out by the second stage of the process, now to be described. The second stage of the process is only carried out when the first part of the process indicated that a defect is present which is not a break-type defect. Such an indication is fed by line 132 to control unit 114.

Initially, gate 110 (FIG. 7) is open so as to feed the data shown in FIG. 8A into the store 100 through the inverter 112. However, during this process, a notional "frame" is set up in the store 100, this frame being shown dotted at 124 in FIG. 8H. Without the frame 124, the inverting effect of inverter 112 would be such that the image stored in store 100 (in response to input of the image of FIG. 8A) would consist of "light" areas corresponding to the metal paths 52A, with the remainder of the store storing a "dark" area. However, the effect of the frame 124 is such as to limit the extent of the "dark" area and the result is therefore that the image stored in store 100 is as shown in FIG. 8I. The metal paths 52A do now not appear but, instead, two dark areas or features 134A and 134B appear, thus representing that part of the area within the frame 124 (FIG. 8H) in which the metal paths 52A are absent. Counter 116 now counts the number of features in the store 100 and will reach a counter of two which will be input into the counter store 118. The counter is reset.

The control unit 114 now opens gate 104 and the data corresponding to the pin hole of FIG. 8B is input into the store 100 in superimposition on the data already there. The result is therefore that the image shown in FIG. 8J is now stored in store 100. Counter 116 is activated to count the number of features and will now reach a count of three, that is, an increase of one. This is noted by the counter store 118.

Store 100 is then cleared and the data (8A) stored in store 10 is re-input into store 100 through gate 110 and inverter 112, thus again producing the image shown in FIG. 8I in the store 100. Counter 116 counts the number of features and the counter store 118 thus records the count of two again. Store 60 now inputs the image shown in FIG. 8C through gate 104 and the result is that store 100 now stores the image shown in FIG. 8K. Counter 116 is re-activated to count the number of features and will still count two features, because the nick 130B will appear as being joined onto the feature 126A. The counter store 118 therefore records no change in the number of features.

In this way, therefore, the indicator 122 receives an indication from the counter store 118 during the first stage of the process to indicate when a defect being inspected is a break-type defect and receives indications during the second stage of the process to indicate whether a defect being inspected is a pin-hole or an intrusion. A size measuring unit 138 is provided for carrying out the same function as the size measuring unit 96 of FIG. 5. As before, the indicator 122 may take any convenient form. The reason for carrying out the process described above with reference to FIG. 7 in two stages will be apparent by considering what would be the result of continuing the second stage further (so as to attempt to use it to classify the break-type defect 130C of FIG. 8D).

Initially, store 100 would be cleared and the data in store 10 (FIG. 8A) re-entered through gate 110 and inverter 112, again producing the image shown in FIG. 8I. The counter 116 would count the number of features, and the counter store 118 would therefore again record a count of two. The counter would be reset. The data representing the image shown in FIG. 8D would then enter into store 100 through gate 104 and the result would be that the image now stored in store 100 would be as shown in FIG. 8L. Counter 116 would now re-count the number of features, thus still producing a count of two, because the defect 130C of FIG. 8D would merely have the effect of acting as a "bridge" between two parts of the same feature 126A. Therefore, the counter store 118 would be unable to distinguish between a break-type error and an intrusion-type defect.

It will be appreciated that although two Figures, FIGS. 5 and 7, have been used to describe the classification operations, it may well be possible to use a large amount of common equipment for carrying out processes of the two Figures.

Many modifications may be made to the system described without departing from the scope of the invention. For example, although in the systems described with reference to FIGS. 5 and 7, it has been stated that each defect is considered separately (that is, input separately into store 80 or store 100), this is not essential and the systems may be modified so that all defects are entered together, the systems being able to consider the separate effect of each defect on the number of features by noting the co-ordinate position of each defect and considering it separately.

What is claimed is:

1. An image inspection system, comprising
   comparison means automatically responsive to the said image and to a desired form thereof whereby to detect abnormalities in the image and to produce data relating thereto,
   storage means operative to store the said data,
   first classifying means responsive to the stored data to classify each abnormality represented thereby as either being an abnormality of addition or an abnormality of omission, and
   second classifying means responsive to the said first classifying means and operative to classify the abnormalities of addition and the abnormalities of omission as being particular types of such abnormalities.

2. A system according to claim 1, including size measuring means responsive to the said data to automatically measure the size of the abnormalities.

3. An image inspection system, comprising
   comparison means responsive to the said image and to a desired form thereof and operative to carry out a rapid inspection of the whole image so as to detect the existence of any abnormalities therein and at least the approximate position of those abnormalities by comparing the actual image with the desired form thereof,
   storage means responsive to the comparison means and connected to store signals corresponding to the detected abnormalities and at least their said approximate positions, and
   inspection means responsive to the stored signals and operative less rapidly to inspect the said detected abnormalities and to classify those abnormalities as to type and to measure their sizes,
   the said inspection means comprising means operative to classify each abnormality as either being an abnormality of addition or an abnormality of omission, and means operative to classify the abnormalities of addition and the abnormalities of omission as being particular types of such abnormalities.

4. A system according to claim 3, in which the comparison means operates in real time.

5. A system according to claim 3 in which each said abnormality is an abnormality which is at least as great in size as a predetermined but variable limit.

6. An image inspection system for inspecting an image in the form of a desired predetermined pattern of image paths with spaces between them, comprising
   comparison means for automatically inspecting the image, the comparison means comprising means for comparing the said image with the desired form of the image and producing data identifying the position and size of each abnormality of addition and of each abnormality of omission,
   storage means for storing the said data,
   first classifying means responsive to the data identifying each abnormality of addition for automatically classifying each such abnormality as an abnormality of addition in a said space and unconnected with any said path, an abnormality of addition in a said space and connected to one said path, or an abnormality of addition in a said space and connected to two said paths, and
   second classifying means responsive to the said data identifying each abnormality of omission for automatically classifying each abnormality of omission as an abnormality of omission within a said path but not completely breaking the path, an abnormality of omission in an edge, only, of a said path, or an abnormality of omission within and completely breaking a said path.

7. A system according to claim 6, including means for measuring the size of each abnormality.

8. A system according to claim 6, in which the image being inspected is the image of a reticle and each said path is a metal path thereon.

9. A method of inspecting an image, comprising the steps of
   rapidly comparing the whole image with a desired form thereof so as to detect the existence of any abnormalities therein and at least the approximate position of those abnormalities and producing data relating to the existence of those abnormalities and their said approximate positions,
   storing the said data,
   processing the stored data so as to carry out a less rapid inspection of those parts of the image where abnormalities have been detected by the comparing step to classify those abnormalities as to type and to measure their sizes,
   classifying each detected abnormality as either being an abnormality of addition or an abnormality of omission, and
   classifying the abnormalities of addition and the abnormalities of omission as being particular types of such abnormalities.

10. A method according to claim 9, in which the comparing step operates in real time but the processing and classifying steps do not.

11. A method of inspecting an image in the form of a predetermined pattern of image paths with spaces between them, comprising the steps of
    automatically comparing the image with a desired form of the image whereby to produce data identifying the position and size of each abnormality of addition and of each abnormality of omission,
    storing the said data,
    automatically processing the said data to classify each abnormality of addition as being either an abnormality of addition in a said space and unconnected with any said path, an abnormality of addition in a said space and connected to one said path, or an abnormality of addition in a said space and connected to two said paths, and
    automatically processing the said data to classify each abnormality of omission as being either an abnormality of omission within a said path but not completely breaking the path, an abnormality of omission in an edge, only, of a said path, or an abnormality of omission within and completely breaking a said path.

12. A method according to claim 11, including the step of measuring the size of each abnormality.

13. A method according to claim 11, in which the image being inspected is the image of a reticle and each said path is a metal path thereon.

* * * * *